United States Patent
Sugiyama et al.

(10) Patent No.: US 8,080,696 B2
(45) Date of Patent: Dec. 20, 2011

(54) METHOD FOR PRODUCING OLEFIN

(75) Inventors: Akinari Sugiyama, Settsu (JP);
Takehiro Chaki, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 12/312,245

(22) PCT Filed: Oct. 26, 2007

(86) PCT No.: PCT/JP2007/070946
§ 371 (c)(1),
(2), (4) Date: Jan. 15, 2010

(87) PCT Pub. No.: WO2008/053811
PCT Pub. Date: May 8, 2008

(65) Prior Publication Data
US 2010/0130797 A1    May 27, 2010

(30) Foreign Application Priority Data
Nov. 1, 2006 (JP) ................................. 2006-297885

(51) Int. Cl.
*C07C 17/25* (2006.01)
(52) U.S. Cl. ....................................... 570/158; 570/156
(58) Field of Classification Search .................. None
See application file for complete search history.

(56) References Cited

U.S. PATENT DOCUMENTS
2,774,798 A    12/1956    Davis et al.

FOREIGN PATENT DOCUMENTS
| JP | 61-5032 | 1/1986 |
| JP | 1-207249 | 8/1989 |
| JP | 11-512110 | 10/1999 |

OTHER PUBLICATIONS

International Search Report dated Jan. 29, 2008 in the International (PCT) Application PCT/JP2007/070946 of which the present application is the U.S. National Stage.
A.Y. Zapevalov et al., "α,α-Disubstituted polyfluoroalkenes", Zhurnal Organicheskoi Khimii, 24(8), pp. 1626-1633, 1988.

*Primary Examiner* — Sudhakar Katakam
(74) *Attorney, Agent, or Firm* — Wenderoth, Lind & Ponack, L.L.P.

(57) ABSTRACT

The present invention provides a method for producing an olefin represented by General Formula (II): $RfCF=CH_2$ (II) (wherein Rf is defined as below), wherein the method includes the step of contacting a fluorohalide represented by General Formula (I): $RfCF_2CH_2X$ (I) (wherein Rf is $H(CF_2)_n$ (n=1 to 8) or $F(CF_2)_n$ (n=1 to 8), and X is Br or I) with a metal in a reaction medium of a polar organic solvent, or a mixed solvent of water and a polar organic solvent to conduct a dehalogenation reaction.

The production method of the present invention provides olefins in a highly selective manner at a low cost and high yield under relatively mild reaction conditions.

2 Claims, No Drawings

METHOD FOR PRODUCING OLEFIN

TECHNICAL FIELD

The present invention relates to a method for producing fluorine-containing olefins, which are useful as a refrigerant, etc.

BACKGROUND ART

A known method for producing olefins is to use zinc or a like metal to eliminate halogen atoms from a hydrocarbon compound that contains at least one halogen atom on each adjacent carbon.

In such a halogen elimination reaction, alcohol and like organic solvents or water is generally used as a reaction medium. When alcohol and like organic solvents are used as a reaction medium, the reaction is performed at a high temperature. Furthermore, the alcohol and like organic solvents need to be separated and recovered from the reaction mixture after the reaction, and this increases costs. When water is used as a reaction medium, the water can be relatively easily separated from the resulting product, but a side reaction tends to occur during the dehalogenation reaction and this lowers the yield of the desired product.

As a result of an extensive study that was conducted on the dehalogenation reaction, it was reported that when water is used as the reaction medium, the side reaction can be reduced by adding polyglycol ether ester of stearic acid, quarternary ammonium salt, or a like hydrocarbon-containing surfactant (see Patent Document 1). However, this method requires using a surfactant in a high concentration, such as 10 wt % to 20 wt %. Because this increases costs and complicates the wastewater treatment, this method is industrially disadvantageous.

Furthermore, when water is used as the reaction medium, the surfactant concentration in the solvent can be reduced to about 0.001 wt % to about 0.1 wt % by using a fluorine-containing surfactant (see Patent Document 2). However, hydrolysis or a like side reaction tends to occur in this method, reducing the yield of the desired product.

Patent Document 1: U.S. Pat. No. 2,774,798
Patent Document 2: Japanese Examined Patent Publication No. 1986-5032

DISCLOSURE OF THE INVENTION

Problem to be Solved by the Invention

The present invention aims to solve the problems of the prior art techniques. One of the main objects of the present invention is to provide a method for producing an olefin by dehalogenating a hydrocarbon compound that contains halogen atoms in an industrially advantageous manner, wherein the olefin is provided in a highly selective manner at a low cost and high yield under relatively mild reaction conditions.

Means for Solving the Problem

The present inventors conducted extensive research to achieve the above object. As a result, they found that when a polar organic solvent or a mixed solvent containing a polar organic solvent and water is used as a reaction medium, the dehalogenation reaction proceeds in a highly selective manner without using a surfactant, providing olefins at a high yield. In particular, when a mixed solvent containing a polar solvent and water with a specific ratio is used as the reaction medium, the dehalogenation reaction proceeds not only in a highly selective manner but also at a relatively low temperature. This makes the method of the present invention a highly advantageous method, from an industrial viewpoint, for producing olefins. Thus the present invention has been completed.

Specifically, the present invention provides the following methods for producing olefins.

Item 1. 1. A method for producing an olefin represented by General Formula (II):

$$RfCF=CH_2 \quad (II)$$

wherein Rf is $H(CF_2)_n$ (n=1 to 8) or $F(CF_2)_n$ (n=1 to 8), the method comprising the step of:

contacting a fluorohalide represented by General Formula (I):

$$RfCF_2CH_2X \quad (I)$$

wherein Rf is the same as above and X is Br or I, with a metal in a reaction medium of a polar organic solvent, or a mixed solvent of water and a polar organic solvent to conduct a dehalogenation reaction.

Item 2. The method according to Item 1, wherein the reaction medium contains not more than 900 parts by volume of water per 100 parts by volume of polar organic solvent.

Item 3. The method according to Item 1, wherein the reaction medium contains 10 to 150 parts by volume of water per 100 parts by volume of polar organic solvent.

In the production method of the present invention, a fluorohalide represented by General Formula: $RfCF_2CH_2X$ (I), wherein Rf is $H(CF_2)_n$ (n=1 to 8) or $F(CF_2)_n$ (n=1 to 8), and X is Br or I is used as a raw material. Specific examples of such fluorohalides include $CF_3CF_2CH_2Br$, $H(CF_2)_4CH_2I$, etc.

The method of the present invention produces an olefin through a dehalogenation reaction by contacting the above-mentioned fluorohalide, which is used as a raw material, with a metal.

Examples of usable metals include magnesium, copper, iron, zinc, tin, antimony and like metals, and alloys of these metals with cadmium, palladium, mercury, etc. These metals may be used singly or in combination. The preferable form of the metal is a powder with an average particle diameter of about 3 μm to about 5 μm, but is not limited to this. It is preferable that the metal powder be used in a condition such that it is sufficiently dispersed in the reaction medium by stirring.

The amount of the metal is not particularly limited. The amount of the metal is preferably about 1 mol to about 2.5 mols per mol of halogen hydrocarbon compound that is used as a raw material.

When conducting the method of the present invention, in order to increase the initial speed of the reaction, zinc chloride, tin chloride, or the like, which are often used for such a purpose, may be added to the reaction system. The amount of the zinc chloride, tin chloride, or the like is generally about 10 parts by weight to about 20 parts by weight per 100 parts by weight of metal, but a larger amount thereof may be used.

In the production method of the present invention, the use of a polar organic solvent, or a mixed solvent that contains water and a polar organic solvent as a reaction medium is an essential feature.

There is no particular limitation to the type of polar organic solvent, and a polar solvent that is compatible with water can be used. For example, solvents represented by the following chemical formulas can be suitably used.

(a) CH$_3$CON(CH$_3$)$_2$
Dimethyl acetamide (b) HCON(CH$_3$)$_2$
Dimethyl formamide (c) CH$_3$OH
Methanol (d) CH$_3$CH$_2$OH
Ethanol (e) CH$_3$CH$_2$CH$_2$OH
Propanol (f) CH$_3$CH(OH)CH$_3$
Isopropanol (g) CH$_3$CH$_2$CH$_2$CH$_2$OH
n-Buthanol (h) (CH$_3$)$_3$COH
t-Buthanol (i) CH$_3$CH$_2$CH$_2$CH$_2$CH$_2$OH
n-Amyl alcohol (j) CH$_3$C(CH$_3$)(CH$_2$CH$_3$)OH
t-Amyl alcohol (k) CH$_3$COOH
Acetic acid (l) CH$_3$COCH$_2$CH$_3$
Ethyl acetate (m) C$_4$H$_8$O
Tetrahydrofuran Among these polar organic solvents, for example, dimethyl acetamide, dimethyl formamide and like amides; and n-amyl alcohol, t-amyl alcohol and like alcohols may be suitably used. If a polar organic solvent is singly used, because the reaction is performed at about 100° C., it is preferable to use polar organic solvents having a boiling point not less than 100° C. when the production method of the present invention is conducted under atmospheric pressure. Examples of such solvents include dimethyl acetamide, dimethyl formamide, n-amyl alcohol, t-amyl alcohol, etc. When the production method of the present invention is conducted under pressure, a polar organic solvent having a boiling point less than 100° C. may be used singly.

The water used as a reaction medium is preferably deionized water, distilled water, etc., but tap water, industrial water, etc., may also be used.

When a mixed solvent containing water and a polar organic solvent is used, the reaction can be conducted at a relatively low temperature by using a mixed solvent that contains not more than 900 parts by volume of water per 100 parts by volume of polar organic solvent. In particular, the selectivity of the dehalogenation reaction can be improved and the reaction can be conducted at a relatively low temperature when the amount of water is preferably about 10 parts by volume to about 150 parts by volume, and more preferably 25 parts by volume to 100 parts by volume, per 100 parts by volume of polar organic solvent. This makes it possible to obtain olefins at a high yield under mild reaction conditions.

In the production method of the present invention, the amount of polar organic solvent or a mixed solvent that contains water and a polar organic solvent, which is used as a reaction medium, is not particularly limited. However, it is preferable that the amount of solvent be sufficient to satisfactorily disperse the metal powder, and it is preferable to use not less than 50 parts by weight and generally about 100 to about 500 parts by weight of the solvent per 100 parts by weight of the fluorohalide that is used as a raw material.

There is no particular limitation to the specific embodiment of the production method of the present invention. An example of the method is to add a metal to a reaction medium and stir the medium to uniformly disperse the metal, and then to add a halogen-containing hydrocarbon compound thereto.

The reaction temperature is generally 0° C. to about 100° C. However, when a mixed solvent of water and a polar solvent is used as a reaction medium, the dehalogenation reaction can be conducted in a highly selective manner under mild conditions with a relatively low temperature of about 10° C. to about 40° C.

The reaction is generally conducted under atmospheric pressure, but may be conducted under pressure. When the reaction is conducted under pressure, for example, the reaction pressure is preferably about 0.2 MPa to about 1 MPa, but is not limited to this.

The above-described method produces olefins in a highly selective manner by dehalogenating a halogen-containing hydrocarbon compound, which is used as a raw material.

Specifically, using the fluorohalide represented by General Formula (I): RfCF$_2$CH$_2$X as a raw material, an olefin represented by General Formula (II): RfCF=CH$_2$ (wherein Rf is the same as above) can be produced at a high yield.

The resulting product may be separated and collected by a standard distillation and rectification method. Alternatively, filtration, liquid separation or the like method may also be employed. It is also possible to collect the product by combining the above methods.

The olefins obtained by the method of the present invention may be, used in various known applications. For example, CF$_3$CF=CH$_2$ is a compound having a low global warming potential and a low ozone depleting potential. Therefore, it is highly useful, for example, as a constituent component and the like for a mixed refrigerant that functions as an alternative to chlorofluorocarbon.

Effect of the Invention

The production method of the present invention makes it possible to produce olefins at a high yield in a simple manner.

In particular, when a mixed solvent that contains water and a polar solvent is used as a reaction medium, the method of the present invention achieves the production of olefins at a high yield under mild reaction conditions.

BEST MODE FOR CARRYING OUT THE INVENTION

The present invention is explained in detail below with reference to Examples.

EXAMPLE 1

A mixed solvent that contains 10 ml of water and 10 ml of dimethyl acetamide (DMAc), and 7.67 g of zinc powder (0.117 mol, average particle diameter: 4.2 μm) were placed in a 100-ml flask equipped with a stirrer, a Dimroth condenser, a dropping funnel, and a thermometer. The mixture in the flask was then stirred well to form a suspension.

To the resulting mixture, 10.3 g (0.048 mol) of $CF_3CF_2CH_2Br$ was added dropwise, followed by a reaction at room temperature (26° C. to 33° C.) for 3.5 hours.

After the completion of the reaction, the resulting reaction mixture was heated and the fraction up to the temperature of 98° C. was extracted. Because the main product ($CF_3CF=CH_2$) had a boiling point of −28.3° C., the main product was collected using a freezing medium consisting of dry ice and acetone. The collected fraction was analyzed with gas chromatography. The result revealed that 99.5 mol % of $CF_3CF=CH_2$ was contained. The yield was 70.1%.

EXAMPLE 2

Using the same reaction apparatus as used in Example 1, a dehalogenation reaction was conducted in the same manner as in Example 1 except that the mixing ratio between water and DMAc was changed and the reaction temperature was also changed. The main product was $CF_3CF=CH_2$.

Table 1 below shows the reaction conditions, and the selectivity and yield of $CF_3CF=CH_2$.

Table 1 also shows the results of Example 1, which are listed as Experiment No. 2.

TABLE 1

| | Reaction Conditions | | | Results | |
|---|---|---|---|---|---|
| Experiment Number | Water (ml) | DMAc (ml) | Reaction Temperature (° C.) | Selectivity (%) | Yield (%) |
| 1 | 20 | 0.0 | 43-45 | 97.9 | 40.8 |
| 2 | 10 | 10 | 26-33 | 99.5 | 70.1 |
| 3 | 4 | 16 | 26-33 | 99.6 | 88.6 |
| 4 | 0 | 20 | 98-100 | 99.9 | 73.8 |

EXAMPLE 3

A mixed solvent containing 10 ml of water and 10 ml of DMAc, and 2.21 g of zinc powder (0.034 mol, average particle diameter: 4.2 μm) were placed in the same kind of apparatus as used in Example 1, and stirred well to form a suspension.

To the mixture, 5.12 g (0.015 mol) of $H(CF_2)_4CH_2I$ was added dropwise, followed by a reaction at room temperature (26 to 33° C.) for 3.5 hours.

After the completion of the reaction, the reaction mixture was heated and the fraction up to the temperature of 98° C. was extracted. Because the main product ($H(CF_2)_3CF=CH_2$) had a boiling point of 32° C., the main product was collected using a freezing medium consisting of ice and water. The collected fraction was analyzed with NMR. The result revealed that 96.3 mol % of $H(CF_2)_3CF=CH_2$ was contained. The yield was 43.3%.

COMPARATIVE EXAMPLE 1

An aqueous solution (20 ml) that contained 0.01 wt % fluorine-containing surfactant represented by the following formula:

and 7.66 g of zinc powder (0.117 mol, average particle diameter: 4.2 μm) were placed in the same kind of apparatus as used in Example 1, and stirred well to form a suspension.

To the mixture, 10.3 g (0.048 mol) of $CF_3CF_2CH_2Br$ was added dropwise, followed by a reaction at room temperature (27° C. to 29° C.) for one hour.

After the completion of the reaction, the reaction mixture was heated and the fraction up to the temperature of 98° C. was extracted. Because the main component ($CF_3CF=CH_2$) had a boiling point of −28.3° C., the main component was collected using a freezing medium consisting of dry ice and acetone. The collected fraction was analyzed with gas chromatography. The result revealed that 87.4 mol % of $CF_3CF=CH_2$ was contained. The yield was 15.4%. It also revealed that 2.27 mol % $CF_3CF_2CH_3$ and 10.4 mol % $CF_3CF_2CH_2OH$ were produced as by-products.

As is clear from the results of Comparative Example 1, when water that contained a fluorine-containing surfactant was used as a reaction medium, both the yield and selectivity were lower than those of Examples 1 and 2 wherein DMAc, or a mixed solvent of DMAc and water was used as a reaction medium.

EXAMPLE 4

In the same apparatus as used in Example 1, 20 ml of DMAc and 7.86 g of zinc powder (0.120 mol) were placed and stirred well to form a suspension.

To the mixture, 13.12 g of $CF_3CF_2CH_2I$ (purity: 96.0%, 0.0484 mol) was added dropwise. The formation of $CF_3CF=CH_2$ was confirmed from the temperature of 60° C., and the mixture was reacted at 75° C. for 30 minutes.

After the completion of the reaction, the reaction mixture was heated to reflux at 98° C. for 30 minutes, and then the fraction was extracted. Because the main product ($CF_3CF=CH_2$) had a boiling point of −28.3° C., the main product was collected using a freezing medium consisting of dry ice and acetone. The collected product was analyzed with gas chromatography. The result revealed that 88.0% of $CF_3CF=CH_2$ was contained. The yield was 49.5%.

EXAMPLE 5

A mixed solvent of 10 ml of water and 10 ml of DMAc, and 7.86 g of zinc powder (0.120 mol) were placed in the same apparatus as used in Example 1, and stirred well to form a suspension.

To the mixture, 13.03 g (0.0484 mol) of $CF_3CF_2CH_2I$ (purity: 96.6%) was added dropwise. The formation of $CF_3CF=CH_2$ was confirmed at room temperature, and the mixture was reacted at 35° C. for 30 minutes.

After the completion of the reaction, the reaction mixture was heated to reflux at 98° C. for 30 minutes, and then the fraction was extracted. Because the main product ($CF_3CF=CH_2$) had a boiling point of −28.3° C., the main product was collected using a freezing medium consisting of dry ice and acetone. The collected product was analyzed with gas chromatography. The result revealed that 96.8% of $CF_3CF=CH_2$ was contained. The yield was 80.8%.

EXAMPLE 6

In the same apparatus as used in Example 1, 20 ml of t-amyl alcohol and 7.70 g (0.118 mol) of zinc powder were placed and stirred well to form a suspension.

To the mixture, 10.24 g (0.046 mol) of $CF_3CF_2CH_2Br$ (purity: 95.7%) was added dropwise. The formation of $CF_3CF=CH_2$ was confirmed at about 90° C. The mixture was reacted for 30 minutes under reflux at 95° C., and then the fraction was extracted. Because the main product ($CF_3CF=CH_2$) had a boiling point of −28.3° C., the main product was collected using a freezing medium consisting of dry ice and acetone. The collected product was analyzed with gas chromatography. The result revealed that 98.9% of $CF_3CF=CH_2$ was contained. The yield was 54.9%.

EXAMPLE 7

A mixed solvent containing 10 ml of water and 10 ml of t-amyl alcohol, and 7.73 g (0.118 mol) of zinc powder were placed in the same apparatus as used in Example 1, and stirred well to form a suspension.

To the mixture, 10.09 g (0.045 mol) of $CF_3CF_2CH_2Br$ (purity: 95.7%) was added dropwise. The formation of $CF_3CF=CH_2$ was confirmed at room temperature, and the mixture was reacted at 30° C. to 40° C. for 30 minutes.

After the completion of the reaction, the reaction mixture was heated to reflux at 85° C. for 30 minutes, and then the fraction was extracted. Because the main product ($CF_3CF=CH_2$) had a boiling point of −28.3° C., the main product was collected using a freezing medium consisting of dry ice and acetone. The collected fraction was analyzed with gas chromatography. The result revealed that 98.6% of $CF_3CF=CH_2$ was contained. The yield was 78.3%.

EXAMPLE 8

In the same apparatus as used in Example 1, 20 ml of dimethyl formamide (DMF) and 7.65 g (0.117 mol) of zinc powder were placed and stirred well to form a suspension.

To the mixture, 10.40 g (0.047 mol) of $CF_3CF_2CH_2Br$ (purity: 95.7%) was added dropwise. The formation of $CF_3CF=CH_2$ was confirmed at 98° C., the mixture was reacted at 100±5° C. for 30 minutes, and then the fraction was extracted. Because the main product ($CF_3CF=CH_2$) had a boiling point of −28.3° C., the main product was collected using a freezing medium consisting of dry ice and acetone. The collected fraction was analyzed with gas chromatography. The result revealed that 99.8% of $CF_3CF=CH_2$ was contained. The yield was 49.0%.

EXAMPLE 9

A mixed solvent containing 10 ml of water and 10 ml of dimethyl formamide (DMF), and 7.69 g (0.118 mol) of zinc powder were placed in the same apparatus as used in Example 1, and stirred well to form a suspension.

To the mixture, 10.41 g (0.047 mol) of $CF_3CF_2CH_2Br$ (purity: 95.7%) was added dropwise. The formation of $CF_3CF=CH_2$ was confirmed at room temperature, and the mixture was reacted at 30° C. to 40° C. for 30 minutes.

After the completion of the reaction, the reaction mixture was heated to reflux at 98° C. for 30 minutes, and then the fraction was extracted. Because the main product ($CF_3CF=CH_2$) had a boiling point of −28.3° C., the main product was collected using a freezing medium consisting of dry ice and acetone. The collected fraction was analyzed with gas chromatography. The result revealed that 98.9% of $CF_3CF=CH_2$ was contained. The yield was 66.0%.

Table 2 below shows the reaction conditions of Examples 8 to 11, and the selectivity and yield of $CF_3CF=CH_2$.

TABLE 2

| Example Number | Reaction Conditions | | | Results | |
| --- | --- | --- | --- | --- | --- |
| | Water (ml) | Polar solvent | Reaction Temperature (° C.) | Selectivity (%) | Yield (%) |
| 6 | 0 | t-Amyl alcohol 20 ml | 90-95 | 98.9 | 54.9 |
| 7 | 10 | t-Amyl alcohol 10 ml | 30-40 | 98.6 | 78.3 |
| 8 | 0 | DMF 20 ml | 95-105 | 99.8 | 49.0 |
| 9 | 10 | DMF 10 ml | 30-40 | 98.9 | 66.0 |

EXAMPLE 10

A mixed solvent containing 24 ml of water and 36 ml of DMAc, and 22.1 g (0.338 mol) of zinc powder were placed in a 300-ml autoclave equipped with a pressure gauge, a thermometer, a degassing valve, and a safety valve, and then stirred well using a magnetic stirrer.

The above-described apparatus was connected to a 75-ml cylinder having 31.16 g (0.132 mol) of $CF_3CF_2CH_2Br$ (purity: 90.4%) placed therein. A closed-system apparatus was set up, and the air in the apparatus was removed using a vacuum pump.

After the above-described operation was completed, $CF_3CF_2CH_2Br$ was gradually added dropwise from the cylinder to a suspension containing water, DMAc and zinc powder at 30° C. in such a manner that the temperature of the reaction vessel could be maintained at 30° C. to 40° C. After completing the addition, a reaction was conducted at 30° C. and 0.4 MPa for 2 hours.

After the completion of the reaction, the reaction vessel was heated and the gas component in the reaction vessel was collected at 50° C. Because the main product ($CF_3CF=CH_2$) had a boiling point of −28.3° C., the main product was collected using a freezing medium consisting of dry ice and acetone. The collected product was analyzed with a gas chromatography. The result revealed that 99.8% of $CF_3CF=CH_2$ was contained. The yield was 87.9%.

The invention claimed is:

1. A method for producing an olefin represented by Formula (II):

$$RfCF{=}CH_2 \qquad (II)$$

wherein Rf is $H(CF_2)_n$ (n=1 to 8) or $F(CF_2)_n$ (n=1 to 8), the method comprising the step of:
contacting a fluorohalide represented by Formula (I):

$$RfCF_2CH_2X \qquad (I)$$

wherein Rf is the same as above and X is Br or I, with a metal in a reaction medium of a mixed solvent of water and a polar organic solvent at a temperature of 10 to 40° C. to conduct a dehalogenation reaction, wherein the reaction medium contains not more than 900 parts by volume of water per 100 parts by volume of polar organic solvent.

2. The method according to claim 1, wherein the reaction medium contains 10 to 150 parts by volume of water per 100 parts by volume of polar organic solvent.

* * * * *